United States Patent [19]

Nayak

[11] Patent Number: 4,789,628

[45] Date of Patent: Dec. 6, 1988

[54] DEVICES FOR CARRYING OUT LIGAND/ANTI-LIGAND ASSAYS, METHODS OF USING SUCH DEVICES AND DIAGNOSTIC REAGENTS AND KITS INCORPORATING SUCH DEVICES

[75] Inventor: P. N. Nayak, Yarmouth, Me.

[73] Assignee: VXR, Inc., Portland, Me.

[21] Appl. No.: 874,541

[22] Filed: Jun. 16, 1986

[51] Int. Cl.$^4$ .................. B01N 33/549; B65D 69/00; B01L 3/00; G01N 1/10

[52] U.S. Cl. ........................................ 435/7; 422/58; 422/61; 422/68; 422/102; 356/246; 435/805; 435/810; 436/518; 436/531; 436/532; 436/800; 436/808; 436/809; 436/810

[58] Field of Search ............... 436/518, 531, 532, 800, 436/808, 809, 810; 435/7, 805, 810; 356/246; 422/58, 68, 102, 61

[56] References Cited

U.S. PATENT DOCUMENTS

| | | | |
|---|---|---|---|
| 4,090,849 | 5/1978 | Healy et al. | 23/253 |
| 4,146,365 | 3/1979 | Kay et al. | 436/809 |
| 4,147,752 | 4/1979 | Suovahiemi et al. | 436/804 |
| 4,197,287 | 4/1980 | Piasio et al. | 436/518 |
| 4,197,361 | 4/1980 | Hoff et al. | 424/8 |
| 4,225,575 | 9/1980 | Piasio et al. | 436/518 |
| 4,280,992 | 7/1981 | Sugiura et al. | 424/1 |
| 4,317,810 | 3/1982 | Halbert et al. | 436/531 |
| 4,599,315 | 7/1986 | Tevasaki et al. | 436/809 |
| 4,628,036 | 12/1986 | Scheepens et al. | 436/808 |
| 4,661,460 | 4/1987 | Sakuma | 356/246 |

*Primary Examiner*—Christine M. Nucker
*Attorney, Agent, or Firm*—David G. Conlin; Linda M. Buckley

[57] ABSTRACT

This invention relates to devices and to methods, diagnostic reagents and kits embodying such devices for use in ligand/anti-ligand assays and the qualitative or semi-quantitative detection of a substance of interest thereby through use of light or photon detecting systems such as reflectometers, colorimeters, fluorimeters and the human eye. Such devices, methods and kits have applications in the biologic research and medical fileds for assaying drugs, hormones, peptides, proteins, enzymes, nucleic acids, antibodies, haptens, antibiotics, viri, infectious agents, tumor markers and the like, in the laboratory, the physicians' office, the veterinarian's office and the home.

26 Claims, 1 Drawing Sheet

DEVICES FOR CARRYING OUT LIGAND/ANTI-LIGAND ASSAYS, METHODS OF USING SUCH DEVICES AND DIAGNOSTIC REAGENTS AND KITS INCORPORATING SUCH DEVICES

FIELD OF THE INVENTION

This invention relate to devices for assaying samples for the presence or absence of a substance of interest, to qualitative and semi-quantitative methods of using such devices and to diagnostic reagents and kits incorporating such devices. Such devices, methods, diagnostic reagents and kits have applications in the biologic research and medical fields for assaying drugs, hormones, peptides, proteins, enzymes, nucleic acids, antibodies, haptens, antibiotics, viri, infectious agents, tumor markers and the like, in the laboratory, the physicians' office, the veterinarian's office and the home.

More particularly, this invention relates to devices and methods, diagnostic reagents and kits embodying such devices for use in ligand/anti-ligand assays and the qualitative or semi-quantitative detection of a substance of interest thereby through use of light or photon detecting systems such as reflectometers, colorimeters, fluorimeters and the human eye.

BACKGROUND OF THE INVENTION

Techniques for assaying a sample for the presence and/or concentration of specific substances are known to those skilled in the art. Examples of such techniques include nucleic acid hybridization assays, various protein-binding methodologies including radioimmunoassay, enzyme immunoassay, enzyme-linked immunoassays. All of these techniques involve the binding of a compound to some sort of specific receptor and accordingly fall into the general category of ligand/anti-ligand assays, a category not limited to any special type of interaction occurring in the assay or to any particular type of components participating in the reaction.

All ligand/anti-ligand assays are based on two premises: (1) that certain pairs of substances (the ligand and the anti-ligand) have a strong and specific affinity for each other, that is, they will tend to bind to each other, while binding little or not at all to other substances; and (2) that methods and devices can be developed that allow detection of ligand/anti-ligand binding interactions once complexes have formed. As used herein, ligand is defined as the substance to be detected, and anti-ligand as the substance used to probe for the presence of the ligand.

Ligand/anti-ligand reactions can be detected by a variety of methods, using various markers to label either the ligand or anti-ligand to permit detection of the reaction product. Currently, the most commonly used markers include enzymes and fluorochromes and radioactive compounds. Immobilization of either the ligand or anti-ligand will facilitate detection in many cases.

Ligand/anti-ligand assays can be generally classed into two categories, heterogeneous and homogeneous. Heterogeneous assays require separation of the bound-labeled component from the free-labeled component prior to detection of the reaction product. Homogeneous assays do not require such a separation step. These assays can further be (1) competitive, for example, where ligand competes for labeled anti-ligand with a solid-phase ligand or where anti-ligand competes with labeled anti-ligand for a solid-phase ligand or (2) non-competitive where there is a direct relationship between label and ligand or anti-ligand.

Ligand/anti-ligand assay methods can be applied to fluorescent immunoassay, enzyme immunoassay and radioimmunoassay techniques to detect the presence or absence of antibodies or antigens, i.e., the ligand, in a sample. In recent years the use of enzyme immunoassays (EIA) and enzyme-linked immunoassays (ELISA) has become increasingly important for the qualitative and semi-quantitative detection of a wide variety of substances. In ELISA methodology, antigens can be labeled directly or indirectly by use of enzyme-labeled antibodies which, under appropriate conditions, catalyze a reaction with a substrate. The enzyme activity is detected by formation of a colored reaction product i.e., a colored end point that may be easily detected by eye or measured by spectroscopic or reflectance means. Several enzymes, including alkaline phosphatase, horseradish peroxidase (HRP) and glucose oxidase, have been coupled to both antigen and antibody. HRP is commonly used and several substrates are available for it. For visual detection in an HRP assay, the substrate will usually comprise a solution of a peroxide such as hydrogen peroxide and a chromogenic material such as o-phenylenediamine or tetramethylbenzidine which manifests a color upon oxidation.

In fluorescent immunoassay techniques antigens can be labeled either directly or indirectly with fluorochrome-labeled antibodies. Fluorochromes are dyes that absorb radiation (e.g., ultraviolet light), are excited by it, and emit light (e.g., visible light). The most commonly used fluorochromes are fluorescein isothiocyante and tetramethylrhodamine isothiocyanate.

Ligand/anti-ligand assays also include protein binding assays wherein a specific binding protein is used as an anti-ligand to probe a sample for the protein which it binds. The reaction product of such protein-binding assays, can also be detected using radioactive, fluorescent or enzyme labels. Either the binding protein or its target protein may be labeled.

Yet another ligand/anti-ligand assay that is becoming increasingly important is the nucleic acid hybridization assay, e.g., the DNA probe assay, which uses a "probe" strand of nucleic acid as an anti-ligand to test for the presence of a complementary DNA sequence. DNA probe assays, like immunoassays, often use radioactive labels, fluorescent labels or enzyme labels. Both immunoassays and DNA probe assays have used luminescent labels as well.

In many cases, ligand/anti-ligand techniques require large sample volumes, are time consuming and involve multi-step procedures. For these reasons, it is desirable to carry out such assays with the aid of a device which facilitates the reaction between ligand and anti-ligand, for example, by using a minimum amount of sample, requiring fewer steps, and enabling the reaction to take place rapidly, within the device without transfer of the ligand being assayed. It is also desirable to carry out such assays with the aid of a device which facilitates detection of the reaction product, in some cases, by eliminating the need for detection equipment or by providing the reaction product in a form which is detectable by equipment without further processing of the reaction product.

Immobilization of either the ligand or anti-ligand will facilitate detection in many ligand/anti-ligand assays. Useful ligand/anti-ligand assay systems for assaying drugs, hormones, peptides, proteins, enzymes, nucleic acids, antibodies, haptens, antibiotics, viri, infectious agents, tumor markers and the like commonly are solid phase systems using ligands or anti-ligands immobilized on a water-insoluble carrier such as metal, glass, or plastic.

U.S. Pat. No. 4,090,849 provides a diagnostic device for the detection of biological particles wherein a metal sheet is used as the solid phase upon which a layer of protein is applied.

U.S. Pat. No. 4,280,992 provides immunologically active substance-frosted glass conjugates for use in assays of physiologically active substances using the same. The glass solid phase of '992 is frosted by physical means, e.g., sandblasting, or by chemical treatment, e.g., etching. '992 teaches use of these glass conjugates in the form of frosted tubes and beads.

The ability of proteins to absorb to plastic materials is a well-known phenomenon to those skilled in the art, and various ligand/anti-ligand assays have been developed in which a protein is immobilized on plastic.

U.S. Pat. No. 4,197,361 discloses an immunoassay for the sandwich technique in which antibody (or antigen) is bound to a plastic, and after reaction with a test sample and then fluorescently tagged antibody (or antigen), fluorescense is read directly from the strip in a fluorometer. '361 further discloses sandblasting the plastic strip to increase the surface area.

Assays have also been developed wherein groups reactive with a particular type of ligand or anti-ligand are grafted to the surface of the plastic. U.S. Pat. No. 4,317,810 discloses a water insoluble polymeric matrix which has a layer of reactive groups grafted onto its opposing surfaces, wherein the surfaces have a designed configuration in the form of a plurality of ridges and depressions so that when the matrix is placed in a vial containing solution both surfaces will be substantially in complete contact with the solution and there will be a minimum of surface-to-surface contact between the matrix and the bottom of the vial.

Although presently available test devices have provided means to increase the sensitivity and ease of carrying out ligand/anti-ligand assays, more sensitive and easier assays are needed. Thus, alternative devices are being sought which require, for example, smaller amounts of sample and fewer steps, and which provide a more convenient methodology.

SUMMARY OF THE INVENTION

The present invention provides devices and methods, diagnostic reagents and kits embodying such devices for the qualitative and quantitative assay of samples for the presence of ligands by forming within the device the reaction product of a ligand and at least one anti-ligand therefor. Carrying out ligand/anti-liquid assays in accordance with the present invention provides assays of improved sensitivity. Furthermore, use of such device facilitates the washing steps in such assays.

Devices according to the present invention for assaying a sample for the presence of a ligand by forming within the device a reaction product of the ligand with at least one anti-ligand therefor comprise: a plastic member defining at least one well having a bottom; a plurality of spaced projections extending upward from the well bottom to increase the surface area thereof the projections being spaced to define interconnecting channels therebetween. In preferred embodiments the projections are pyramidal, columnar, conical, rectangular, cylindrical or dome-shaped.

The number and dimensions of wells defined by the plastic member 5 will depend upon the nature of the assay to be conducted. In some embodiments of the present invention the well bottom further comprises a ligand or anti-ligand. In yet other embodiments the well bottom further comprises a chromogen. In yet other embodiments the well bottom comprises reactive groups.

Devices according to the present invention and methods, diagnostic reagents and kits incorporating such devices, can be used for carrying out a variety of ligand-/anti-ligand assays provided that the reaction product of a ligand and at least one anti-ligand therefor can be immobilized in the well. In general the ligand/anti-ligand reaction product is formed in the well bottom and is detected by methods well known to those skilled in the art. For example, in carrying out ligand/anti-ligand assays according to the present invention either a ligand or anti-ligand may be immobilized in the well. Accordingly, the present invention provides devices, and diagnostic reagents and kits incorporating such devices, for carrying out competitive assays wherein a ligand is immobilized in a well and sample ligand competes with immobilized ligand for labeled anti-ligand. The present invention also provides devices, and diagnostic reagents and kits incorporating such devices, for carrying out (i) competitive assays wherein the anti-ligand is immobilized and sample ligand competes with labeled ligand for the immobilized anti-ligand; (ii) sandwich assays wherein a first anti-ligand, immobilized on a membrane, captures a ligand and a second anti-ligand reacts with the immobilized ligand to form a reaction product capable of being detected; and (iii) assays where, e.g., a bacterial cell or virus, is immobilized on the surface of the well and the RNA or DNA is subsequently extracted therefrom and also immobilized in or on the membrane.

Devices according to the present invention may also be used advantageously in enzyme-amplified immunoassays. (See, e.g., Stanley, C. J. et al., *Am. Clin. Prod. Rev.* October, 1985, P. 34) In its simplest form, the enzyme label in an immunoassay (the primary system) is used to provide a trigger substance for a secondary system that can generate a large quantity of colored product. The enzyme-amplified immunoassay differs from the conventional type in that the product from the enzyme label need not, in itself, be measurable but can instead act catalytically on the secondary system.

Enzyme-channeling immunoassays such as that described by Litman, D. J. et al., *Clin. Chem.* (1983) 29:1598, are another example of ligand/anti-ligand assays which may be conducted using devices according to the present invention, and diagnostic reagents and kits embodying such devices. The Litman et al. assay involves sequential enzyme reactions catalyzed by the glucose oxidase/horseradish peroxidase channeling pair wherein the ligand/anti-ligand reaction product is an insoluble chromophore.

Accordingly, the present invention provides a method for assaying one or more samples for the presence of at least one ligand with the aid of a device for assaying one or more samples for the presence of a ligand by forming within the device a reaction product of the ligand with at least one anti-ligand therefor and detecting the reaction product, the device comprising: a plastic member defining at least one well having a bottom, the well comprising at least one anti-ligand; and a plurality of spaced projections extending upward from the well bottom to increase the surface area thereof, the projections being spaced to define interconnecting channels therebetween; the method comprising: (1) introducing the sample into the well bottom; (2) forming in the well bottom a ligand/anti-ligand reaction product; and (3) detecting the ligand/anti-ligand reaction product. In yet other embodiments the well bottom comprises at least one ligand and the method comprises: (1) introducing the sample into the well bottom; (2) forming in the well bottom a ligand/anti-ligand reaction product; and (3) detecting the reaction product.

The devices, and diagnostic reagents of the present invention may be used in the production of kits for assaying a sample for the presence of a ligand. For example, one kit according to the present invention comprises the following in combination: a device, in accordance with the present invention, for assaying one or more samples for the presence or absence of at least one ligand by forming within the device a reaction product of the ligand with at least one anti-ligand, the device comprising: a plastic member defining at least one well having a bottom, the well bottom comprising a first anti-ligand; and a plurality of spaced projections extending upward from the well bottom to increase the surface area thereof, the projections being spaced to define interconnecting channels therebetween; a first anti-ligand immobilized in the well bottom; and a second anti-ligand capable of being detected.

One kit for an ELISA according to the present invention comprises in combination a first antibody immobilized in the well bottom; a second antibody conjugated with an enzyme; a substrate for the enzyme; and a chromogen. In one such ELISA, the enzyme comprises horseradish peroxidase, the chromogen comprises tetramethylbenzidine, and the substrate comprises hydrogen peroxide.

In yet other embodiments of kits according to the present invention, the kit comprises the following in combination: a device for assaying one or more samples for the presence or absence of at least one ligand by forming within the device a reaction product of the ligand with at least one anti-ligand, the device comprising: a plastic member defining at least one well, the well comprising a ligand; and a plurality of spaced projections extending upward from the well bottom, the projections being spaced to define interconnectiong channels therebetween; and a ligand capable of being detected e.g. for competitive binding assays. In yet other embodiments for competitive binding assays the ligand rather than the antiligand is bound to the well and the anti-ligand is provided in the kit in a form capable of being detected.

Kits for enzymic inhibition assays, another type of ligand/anti-ligand assay, are also encompassed in the present invention. In such embodiments of the kit the well bottom comprises an enzyme, and a solution of an anti-ligand is provided which binds near the active site of the enzyme. The presence of bound ligand inhibits product formation from a substrate.

Thus, it is seen that devices, methods and kits according to the present invention are particularly suitable for qualitatively and quantitatively detecting a reaction product of a ligand with at least one anti-ligand therefor wherein the reaction product is detectable by a color change or production, or the emission or change in emission of light, e.g., luminesence, or fluoresence or phosphorescence. The configuration of these devices is such that assays may be carried out completely within the device, if desired, thus eliminating the additional step of removing the sample for measurement.

BRIEF DESCRIPTION OF THE DRAWINGS

A further understanding of the invention may be had by referring to the accompanying drawings, wherein.

DETAILED DESCRIPTION OF THE INVENTION

Figure 1:
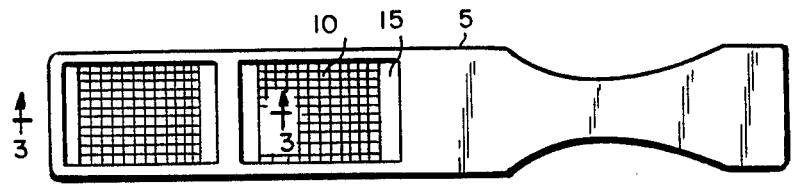
FIG. 1 is a plan view of one embodiment of a device according to the present invention.
Figure 2:
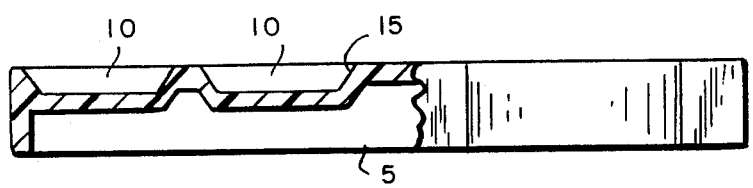
FIG. 2 is a side view, partially in section, of FIG. 1.
Figure 3:
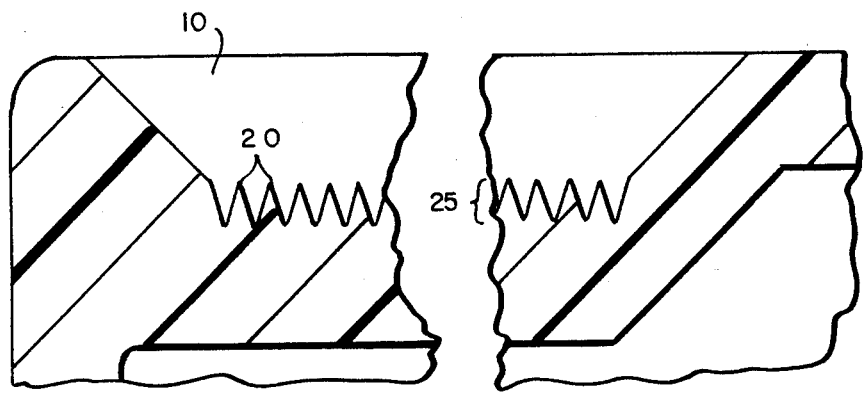
FIG. 3 is an enlarged view of a section of the well bottom of FIG. 1 along line 3—3 of FIG. 1.
Figure 4:
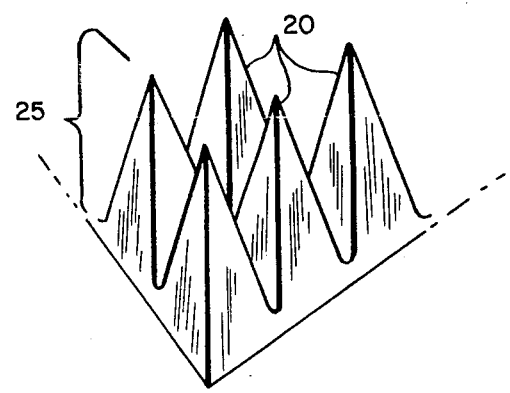
FIG. 4 is an enlarged isometric view of a well bottom showing pyramidal projections.

Referring to the drawings, FIGS. 1, 2, 3 and 4 illustrate a device according to the present invention for assaying a sample for the presence of a ligand by forming within the device a reaction product of the ligand with at least one anti-ligand therefor, said device comprising a plastic member 5 defining two wells 10; and a plurality of spaced pyramidal projections 20 extending upward from the well bottom 25, the projections being spaced to form interconnecting channel therebetween.

The plastic member 5 may be selected from a variety of plastic materials. The material of choice will be determined by the nature of the assay to be carried out, e.g., ability to bind the ligand or anti-ligand. In preferred embodiments, the material will be a plastic selected from the group polyethylene, polypropylene, polystyrene, polycarbonate, polysulfone, polymethylmethacrylate or any plastic that can be molded or otherwise formed to a desired shape. A preferred plastic in the streptoccus A assay of Example I below is polymethylmethacrylate. In the allergen assay of Example II, polystyrene is a preferred plastic. In embodiments wherein the device is molded, a preferred plastic is a thermoplastic which can be injection molded. In embodiments the plastic member 5 is transulucent or transparent so that a light can be passed through it. For example, if the detection is by a fluorimeter technique, it may be desirable to visualize the sample by exciting from below from a fluorescent light source.

The plastic member 5 may be of any shape which will accommodate a desired number of wells 10. The dimensions, shape, number and positioning of the wells 10 depends, in part, upon the nature of the assay carried out and the means used to detect the reaction product. In some embodiments of the present invention, one or more wells may be used to carry out an assay on a control or comparison sample. In some embodiments of the present invention, the well 10 comprises at least one ligand or anti-ligand. In yet other embodiments the well 10 comprises reactive chemical groups grafted thereto. Techniques for grafting such groups on plastic are well known to those skilled in the art. The well may also comprise a chromogen or a species which emits light or fluoresces under the conditions of the assay.

In a preferred embodiment of the present invention shown in FIGS. 1-4, the projections 20 extending upward from the well bottom 25 are pyramidal. However, the projections may be of any shape which will increase the surface area of the well 10 without creating areas that are hard to wash, e.g., crevices and capillaries. According to preferred embodiments of the present invention the projections are pyramidal, columnar, conical, rectangular, cylindrical or dome-shaped. The projections are spaced to form interconnecting channels therebetween to enable the sample and reagents to spread over the well bottom 25.

Devices according to the present invention offer advantages with respect to increased surface area for binding of the ligand or anti-ligand and reproducibility. It is desirable to increase the surface area of the well bottom 25, so as to maximize formation of reaction product, such as in assays of substances which may be present in low concentration. The surface area of the well bottom in devices according to the present invention can be controlled and thus the amount of ligand or anti-ligand adsorbed or bound can be controlled, to provide for reproducible results from assay to assay. The reaction of ligand with anti-ligand occurs primarily in the volume of liquid contained in the space surrounding the projections.

The depth of the well depends on the total well volume desired. However, increasing the depth makes the surface harder to wash since the geometry becomes more like a tube than a flat surface as the depth of the well increases. It is preferred that liquid sample and other reactants be easily rinsed from the well 10 so that the assay may be carried out rapidly with adequate washing. In preferred embodiments the sides of the well are contoured so that they meet the well bottom at an obtuse angle, i.e., without forming a crevice or capillary which is difficult to wash. In preferred embodiments the wells may be flushed with a continuous stream of reagent. This method of washing offers an advantage over the dilution type of wash that is achieved in a tube configuration. Too low a depth makes the device prone to spills and requires inconveniently small volumes of reagents.

The sides of the well meet the well bottom in a manner to enhance washability. For example, in the embodiment shown in FIGS. 1-4 the sides of the well meet the bottom at an angle so that wash water flows over the well bottom without creating a dead pocket.

In the embodiment of a device according to the present invention shown in FIGS. 1-4 it has been found that a well volume of from 0.05 ml to 0.2 ml is preferred for ligand/anti-ligand assays. With this preferred volume range, a well depth of from 2 to 3 mm is preferred.

The height of the projections is determined from a consideration of the desired sample volume, together with the dimensions of the well bottom. For example, in a rectangular well bottom as shown in FIGS. 1-4 having a 1 cm $\times$ 1 cm size test area, a desirable height for the projections is between 0.05 cm and 0.2 cm. A depth of about 0.1 cm is preferred in some embodiments.

In the embodiment shown in FIGS. 1-4, the surface area enhancement, a function of the ratio of the height to the width of the pyramidal projections, is about 4, with a ratio of about 2. Ratios higher that about 2 or 3, when combined with the height and test area limitations described above, are not practical since the width of the projections would become very small and hard to wash (i.e. they will begin to behave like crevices).

In carrying out assays by means of devices according to the present invention it may be desirable to simultaneously assay in the same device a sample to be tested and one or more control samples to serve as a reference, e.g., in competitive binding ligand/anti-ligand assays and/or to verify that the reagents being used to carry out the assay are functioning properly. In such embodiments, the plastic member will define two or more wells. FIGS. 1-4 show a two well embodiment of the present invention wherein one well may be used to assay a sample to be tested, the other, for example, to assay a control sample.

Devices according to the present invention can be used for any assay procedure wherein the ligand reacts with an anti-ligand therefor to give one or more reaction products which can be immobilized in the well. Accordingly, the present invention provides a method for assaying one or more samples for the presence of a ligand by forming within the device a reaction product of the ligand with at least one anti-ligand therefor and detecting the reaction product, said device comprising: a plastic member defining at least one well having a bottom, the well comprising at least one anti-ligand; and a plurality of spaced projections extending upward from the well bottom to increase the surface area thereof, the projections being spaced to form interconnecting channels therebetween; the method comprising: (1) introducing the sample to the well bottom and forming in the well bottom a ligand/anti-ligand reaction product; (2) forming a detectable reaction product; and (3) detecting the detectable reaction product. In some embodiments step 2 takes place together with Step 1. In yet other embodiments washing steps are included.

Devices, according to the present invention, are particularly useful for qualitatively or semi-quantitatively detecting reaction products of a ligand with an anti-ligand therefor, wherein detection of the reaction product is by a color change, the emission of light or fluorescence.

Ligand/anti-ligand reaction products may be detected, if present in the well bottom, by techniques well known to those skilled in the art. Where the reaction product in the well is detectable by a color change, the sample may be detected by measuring the reflectance of the well bottom using instruments and techniques known to those skilled in the art. The present device is particularly suited for permitting visual detection of reflectance of the well bottom.

Devices according to the present invention are useful for assaying samples for the presence of a variety ligands such as drugs, hormones, peptides and proteins. In a preferred ELISA method according to the present invention, the ligand comprises an antigen and the well bottom further comprises a first antibody; and step 2 comprises the steps of (i) introducing to the well bottom a second antibody conjugated with an enzyme; (ii) allowing the second antibody to react with the antigen/-first antibody reaction product, (iii) washing the well, (iv) introducing a solution comprising a substrate for the enzyme and a chromogen to the well bottom and (iv) detecting, visually or with an appropriate instrument, the reaction product of the first and second antibodies with the antigen. The method may further comprise additional washing steps. A particularly preferred enzyme is horseradish peroxidase and a particularly preferred substrate/chromogen comprises $H_2O_2$ and tetramethylbenzidine.

Thus, we have described and provided examples of unique devices for assaying a sample for the presence of a ligand by forming and detecting a reaction product of the ligand at least one anti-ligand therefor; qualitative and semi-quantitative methods of using such devices; and diagnostic reagents and kits incorporating such devices. The ease with which ligand/anti-ligand assays may be carried out using devices and methods according to the present invention, makes such devices particularly suitable for diagnostic reagents and kits for the home diagnostic market.

This invention will be further understood with reference to the following examples which are purely exemplary in nature and are not meant to limit the scope of the invention.

EXAMPLES

EXAMPLE I

Device Procedure For Detection Streptococcus A Antigen

A strep A assay was established using a device similar to that shown in FIGS. 1–4 by immobilizing antibody in the well in the manner described below. The device was made of molded polymethylmethacrylate.

Group A Streptococcal antigen was simultaneously extracted from a sample of cells and captured by an immobilized antibody therefor. The assay is a solid-phase, two-site, enzyme-liked immunoassay using two polyclonal antibodies, one immobilized on a solid-phase and the other in solution and conjugated to horseradish peroxidase. The polyclonal antibodies were raised in rabbits and prepared using techniques known to those skill in the art. The assay is a qualitative or semi-qualitative procedure.

In this assay, the sample was taken from the throat. The data was run in duplicate. Sample swabs, each containing about $10^6$ bacteria were used to inoculate the test well bottoms. Inoculation of the test well bottoms was accomplished by rolling and rubbing the tip of the swab against the test well bottom (antibody coated), thereby transferring the bacteria to the well. Negative controls were run by adding the same sequence of reagents to uninoculated wells (negative well) as to test wells.

Procedure

1. The specimen was collected on a dacron tipped swab. The swab was then applied to the test well bottom (as described above) coated with a first polyclonal antibody to Group A Streptococca antigen.
    Antigen: Rabbit Anti-Strep A antibody was affinity purified using N-acetyl glucosamine agarose (Sigma Chemical. St. Louis).
    Antibody Coating Devices: The well bottoms were coated with polymerized (0.002% gluteraldehyde) anti-strep A antibody at 5 microgram/well in 250 microliters of PBS with 0.1% azide overnight. The wells were washed once with a phosphate buffer, pH 7, and incubated in a phosphate buffered saline with 4% BSA at pH 7.4 for two hours. The wells were then washed and the devices were ready for use.
2. 50 microliters of reagent A was added to the test and negative control well bottoms followed by 50 microliters of reagent B. Finally, 50 microliters of reagent C was added to the well bottoms. The reagents were constituted as follows:
    Reagent A: sodium nitrite solution was made by adding 138 grams per liter sodium nitrate in distilled water.
    Reagent B: acetic acid solution was made by adding 7.102 milliters of glacial acidic acid to 1 liter of distilled water.
    Reagent C: conjugate solution was made by adding to one liter of distilled water, 10.46 grams per bis tris, 500 milliters per liter conjugate, one milliliter per liter TWEEN 20, pH 6.
    Conjugate: Rabbit Anti-Strep A antibody, affinity purified, and conjugated with HRP using a modification of the Nakane method (P. K. Nakane and A. Kawasi). (J. Histochem. Cytochem. 22, 1084 (1974)).
3. These reagents were incubated for about three minutes.
4. Next, 50 microliters of wash solution was added to each well bottom.
    Wash solution was constituted of the following: 14.09 grams per liter potassium phosphate, monobasic; 60.36 grams per liter potassium phosphate, dibasic; 8.10 grams per liter sodium chloride 90 milliters per liter TRITON×100, Q5 to one liter with distilled water, pH 7.3.
5. The wells were flooded with water and tamped to prevent dilution of the next set of reagents.
6. 100 microliters of reagent D and 50 microliters of reagent E were added to the well bottoms.
    Reagent D is the substrate solution and was constituted of 13.615 grams per liter trihydrous sodium acetate, 0.47 grams per liter urea peroxide, 1.0 molar citric acid solution to pH the solution to pH 5, all dissolved in distilled water.
    Reagent E is a chromogen solution and was made by adding •milliters of methanol to 500 milliters of glycerol and adding 1.27 grams of TMB to that one liter of solution. TMB is 3,3′,5,5′-tetramethylbenzidine.
7. The contents of the wells were incubated for two minutes.
8. To determine the reaction, the color in the test well was noted against the color in the negative well. A dark color in the test well indicated a positive reaction, i.e., the presence of Step A.

EXAMPLE II

Device Procedure for the Detection of Allergens

This is an example of a solid phase protein binding assay. To test for allergic reaction one or more allergen extracts (Ventrex) were immobilized via direct adsorption in the well bottom of a polystyrene device similar to that shown in FIGS. 1 to 4.

The assay procedure was as follows:

1. Allergens were immobilized in the well bottoms by direct adsorption as follows:
    (a) allergen extracts were diluted to a predetermined concentration in a carbonate buffer pH 9.5.
    (b) the coating volume per well bottom was equal to 400 microliters.
    (c) the well being used for the assay's negative control was not coated
    (d) The wells were allowed to coat overnight at room temperature, then washed and dried the next day.
2. Allergen extracts were added to the test well bottoms.
    (a) pollen extract—2 grasses, 2 trees and 2 weeds
    (b) cat/dog extract
    (c) dust mold/mold extract
3. Assay Procedure
    (a) 100 microliters patient sample was added to each test well and negative control well.
    (b) 100 microliters conjugate was added to each well.
    (c) The device was shaken lightly to mix.

(d) The device was covered to prevent evaporation and incubated overnight at room temperature.
(e) The wells were flushed with deionized water.
(f) 3 drops substrate buffer and 3 drops chromogen were added.
(g) The blue color in test well was observed and compared with the color in negative control well. If the test well was darker, the test was positive for 1 or more allergens in the particular well.
(h) materials
1. Enzyme-antibody conjugate used is goat antibody (polyclonal) to human IgE (g'hIgE) (Ventrex) conjugated to horseradish peroxidase (HRP) (Beohringer-Mannheim) via procedures known to those skilled in the art (See, e.g., Nakane procedure, Wilson, B. M. et al., *Immunofluorescense and Related Techniques*, at p. 215, 1978, Elsevier/North-Holland Biomedical Press)
2. Wash solution (0.01M PBS, 0.2% Triton X-100, pH 7.4) (Ventrex).
3. Substrate-chromogen solution (prepared immediately before use): 5(% 0.127% tetramethylbenzidine (Sigma) in absolute methanol (Fischer), 50% 4.7 mM $H_2O_2$ in 0.1M citrate-acetate, pH 5.0) (Ventrex). A blue color indicates binding of IgE in the test liquid to the allergen immobilized on the disc. White indicates the absence of reactive IgE in the liquid.

It is understood that the examples and embodiments described herein are for illustrative purposes only and that various modifications or changes in light thereof that will be suggested to persons skilled in the art are to be included in the spirit and review of this application and the scope of the approved claims.

What is claimed is:

1. A device for assaying a sample for the presence of a ligand by forming within the device a reaction product of the ligand with at least one anti-ligand therefor, said device comprising:
   a plastic member defining at least one well having a bottom; and
   a plurality of spaced projections extending upward from the well bottom to increase the surface area thereof, the projections being spaced to define interconnecting channels therebetween.

2. A device according to claim 1 wherein the projections are pyramidal, columnar, conical, rectangular, cylindrical or dome-shaped.

3. A device according to claim 1 wherein the well further comprises at least one immobilized ligand or anti-ligand.

4. A device according to claim 3 wherein the ligand is a drug, hormone, peptide, protein, enzyme, nucleic acid, antibody, hapten, antibiotic, receptor, virus, hormone or infectious agent.

5. A device according to claim 1 wherein the well bottom comprises one or more immobilized chromogens, luminogens or fluorogens.

6. A device according to claim 1 wherein the plastic member is molded.

7. A device according to claim 1 wherein the plastic member is transparent or translucent.

8. A device according to claim 1 wherein the well bottom further comprises reactive chemical groups grafted thereto.

9. A device according to claim 1 wherein the sides of the well are contoured.

10. A device according to claim 1 wherein the plastic member comprises polyethylene, polypropylene, polystyrene, polycarbonate, polysulfone or polymethylmethacrylate.

11. A device according to claim 1 wherein the capacity of the well bottom is at least 0.05 ml.

12. A device according to claim 1 wherein the surface area of the well bottom is increased by at least a factor of 2.

13. A device according to claim 1 having a plurality of wells.

14. A method for assaying one or more samples for the presence of at least one ligand with the aid of a device for assaying one or more samples for the presence of a ligand by forming within the device a detectable reaction product of the ligand with at least one anti-ligand therefor and detecting the reaction product, the device comprising:
   a plastic member defining at least one well having a bottom, the well comprising at least one immobilized anti-ligand; and
   a plurality of spaced projections extending upward from the well bottom to increase the surface area thereof, the projections being spaced to define interconnecting channels therebetween;
the method comprising:
   (1) introducing the sample into the well; (2) forming in the well a ligand/anti-ligand reaction product; and (3) detecting the ligand/anti-ligand reaction product capable of detection.

15. The method of claim 14, wherein the method further comprises washing the well between one or more steps.

16. A method according to claim 14 wherein the ligand comprises an antigen and the anti-ligand comprises antibody.

17. The method of claim 14 wherein the well bottom comprises a first antibody; and step 3 comprises the steps of:
   (i) adding to the well a solution comprising a conjugate of an enzyme with a second antibody and forming a reaction product comprising the first antibody, the antigen and the second antibody;
   (ii) washing the well; and
   (iii) adding to the well a second solution comprising a substrate for the enzyme which reacts in the presence of the enzyme to produce a color or color change.

18. A method for assaying one or more samples for the presence of at least one ligand with the aid of a device for assaying one or more samples for the presence of a ligand by forming within the device a detectable reaction product of the ligand with at least one anti-ligand therefor and detecting the reaction product, the device comprising:
   a plastic member defining at least one well having a bottom, the well comprising at least one immobilized ligand; and
   a plurality of spaced projections extending upward from the well bottom to increase the surface area thereof, the projections being spaced to define interconnecting channels therebetween; the method comprising:
   (1) introducing the sample into the well; (2) forming in the well a ligand/anti-ligand reaction product; and (3) detecting the reaction product capable of detection.

19. The method of claim 14, wherein the method further comprises washing the well between one or more steps.

20. A method according to claim 14 wherein the ligand comprises an antigen and the anti-ligand comprises an antibody.

21. A kit comprising, in combination:
(a) a device for assaying a sample for the presence of a ligand by forming within the device a reaction product of the ligand with an anti-ligand therefor, said device comprising:
a plastic member defining at least one well having a bottom, the well comprising an immobilized anti-ligand; and
a plurality of spaced projections extending upward from the well bottom to increase the surface area thereof, the projections being spaced to define interconnecting channels therebetween;
(b) the ligand, wherein the ligand is capable of detection.

22. A kit comprising, in combination:
(a) a device for assaying a sample for the presence of a ligand by forming within the device a reaction product of the ligand with a first and second anti-ligand therefor, said device comprising:
a plastic member defining at least one well having a bottom, the well comprising the first anti-ligand; and a plurality of spaced projections extending upward from the well bottom to increase the surface area thereof, the projections being spaced to define interconnecting channels therebetween; and
(b) a second anti-ligand, the second anti-ligand being capable of detection.

23. A kit comprising, in combination:
(a) a device for assaying a sample for the presence of a ligand by forming within the device a reaction product of the ligand with an anti-ligand therefor, said device comprising:
a plastic member defining at least one well having a bottom, the well comprising at least one ligand; and
a plurality of spaced projections extending upward form the well bottom to increase the surface area thereof, the projections being spaced to define interconnecting channels therebetween; and
(b) an anti-ligand, the anti-ligand being capable of detection.

24. The kit of claim 21, wherein the ligand is detectable by light or radiation emission, absorption or fluoresence or by measuring the amount of light reflected from the well.

25. The kit of claim 22, wherein the second anti-ligand is dectectable by light or radiation emission, absorption or fluoresence or by measuring the amount of light reflected from the well.

26. The kit of claim 24, wherein the anit-ligand is dectectable by light or radiation emission, absorption or fluoresence or by measuring the amount of light reflected from the well.

* * * * *